United States Patent
McHugo

(10) Patent No.: US 10,092,426 B2
(45) Date of Patent: Oct. 9, 2018

(54) NON-FORESHORTENING, AXIAL TENSION CONSTRAINABLE STENT

(75) Inventor: Vincent McHugo, Co. Tipperary (IE)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/480,722

(22) Filed: May 25, 2012

(65) Prior Publication Data

US 2012/0310327 A1     Dec. 6, 2012

Related U.S. Application Data

(60) Provisional application No. 61/491,670, filed on May 31, 2011.

(51) Int. Cl.
    *A61F 2/82*          (2013.01)
    *A61F 2/90*          (2013.01)
    *A61F 2/95*          (2013.01)

(52) U.S. Cl.
    CPC ........ *A61F 2/90* (2013.01); *A61F 2002/9505* (2013.01); *A61F 2002/9528* (2013.01); *A61F 2002/9534* (2013.01); *A61F 2230/0054* (2013.01)

(58) Field of Classification Search
    CPC ...... A61F 2/844; A61F 2/89; A61F 2002/044; A61F 2002/9511; A61F 2002/825; A61F 2/06; A61F 2/82; B21C 23/24
    USPC ...... 623/1.1–3.1; 606/19–192, 194, 198, 200
    See application file for complete search history.

(56) References Cited

U.S. PATENT DOCUMENTS

| | | | | |
|---|---|---|---|---|
| 4,621,638 A | * | 11/1986 | Silvestrini | A61L 17/04 264/178 F |
| 4,655,771 A | * | 4/1987 | Wallsten | 623/1.22 |
| 4,913,141 A | * | 4/1990 | Hillstead | 623/1.11 |
| 5,035,706 A | * | 7/1991 | Giantureo et al. | 606/198 |
| 5,591,230 A | * | 1/1997 | Horn et al. | 623/1.17 |
| 6,221,096 B1 | * | 4/2001 | Aiba et al. | 623/1.11 |
| 6,299,635 B1 | * | 10/2001 | Frantzen | 623/1.17 |
| 6,475,236 B1 | * | 11/2002 | Roubin et al. | 623/1.15 |
| 6,764,503 B1 | * | 7/2004 | Ishimaru | 623/1.11 |
| 7,857,844 B2 | * | 12/2010 | Norton et al. | 623/1.53 |
| 2002/0188344 A1 | * | 12/2002 | Bolea et al. | 623/1.11 |
| 2005/0197690 A1 | * | 9/2005 | Molaei et al. | 623/1.13 |
| 2007/0219626 A1 | * | 9/2007 | Rolando et al. | 623/1.16 |
| 2008/0300668 A1 | * | 12/2008 | Bonsignore | 623/1.15 |
| 2009/0105747 A1 | * | 4/2009 | Chanduszko et al. | 606/200 |
| 2009/0182407 A1 | * | 7/2009 | Leanna et al. | 623/1.11 |

(Continued)

FOREIGN PATENT DOCUMENTS

| EP | 1518518 A1 | * | 3/2005 | | A61F 2/06 |
|---|---|---|---|---|---|
| EP | 1518518 A2 | * | 3/2005 | | A61F 2/06 |

OTHER PUBLICATIONS

Alimaxx-ES stent instructions. MeditMedica Endotek. http://www.endotek.mert.com Wayback machine date Apr. 11, 2010.*

(Continued)

*Primary Examiner* — Yashita Sharma
(74) *Attorney, Agent, or Firm* — Brinks Gilson & Lione

(57) ABSTRACT

Methods and devices for a non-foreshortening, axial tension constrainable stent are illustrated such that a length of the stent in a collapsed state is about equal to the length of the stent in an expanded state which provides for better stent placement, easier repositioning and removal, and reduced stent migration.

17 Claims, 5 Drawing Sheets

(56) References Cited

U.S. PATENT DOCUMENTS

2011/0190865 A1* 8/2011 McHugo et al. ............ 623/1.11
2012/0041538 A1* 2/2012 White et al. ................ 623/1.12

OTHER PUBLICATIONS

Loew, Burr. Nov. 2008. Clinical Endoscopy. Comparitive performance of uncoated, self-expanding metal biliary stents of different designs in 2 diameters: final results of an international multicenter, randomized, controlled trial. Gastrointestinal Endoscopy, vol. 70, Edition 3.*
Superelastic Nitinol Alloys. Material Data Sheet. NDC. www.nitinol.com.*
Elasticum suture. Korpo. 2014.*

* cited by examiner

# NON-FORESHORTENING, AXIAL TENSION CONSTRAINABLE STENT

RELATED APPLICATION

This application claims the benefit of priority from U.S. Provisional Application No. 61/491,670, filed May 31, 2011, and titled "Non-Foreshortening, Axial Tension Constrainable Stent", the contents of which is incorporated herein by reference.

TECHNICAL FIELD

The present invention relates to medical devices and more specifically, stents.

BACKGROUND

Self expanding stents are useful for a variety of procedures requiring the patency of a bodily pathway. Such stents are generally biased to expand, such that when deployed, they assume an open position, pushing outward and into the surrounding area into which deployed. The radial expansion creates a pathway in a once occluded area. However, once deployed, such stents become difficult to remove or reposition when no longer in a collapsed state due to the expandable nature of the stent. Merely pulling or pushing the stent while in an expanded state to reposition or remove it may cause damage, trauma, or destruction of the area in which the stent is placed.

Moreover, self expanding stents, when in an expanded state, generally have a length shorter than when in a collapsed state. This property, known as foreshortening, may result in a stent being deployed in the wrong position because the stent shortens during expansion. Accurate placement of the stent may be important in certain applications, for example to prevent stent migration or to properly open a stricture along the entire length of the stricture.

BRIEF SUMMARY

In a first aspect, a non-foreshortening, axial tension constrainable stent is provided having a proximal portion and a distal portion; a plurality of wires configured in a plurality rows, wherein each row is configured into a plurality of zigzags wherein the rows together comprise a cylindrical shape having a lumen extending between the proximal portion and the distal portion, and wherein each of the plurality of zigzags include a plurality of first apexes pointing towards the proximal portion and a plurality of second apexes pointing towards the distal portion; a plurality of first sutures in communication with the first apexes of the zigzags wherein the proximal-most portions of the first sutures include a plurality of first loops; a plurality of second sutures in communication with the second apexes of the zigzags wherein the distal-most portions of the second sutures include a plurality of second loops; a first purse string suture in communication with the first loops; and a second purse string suture in communication with the second loops; wherein the first purse string suture and the second purse string suture are configured to collapse the plurality of zigzags when an opposite axial force is applied to each of the first purse string suture and the second purse string suture.

In a second aspect, a stent is provided having a stent body formed from a plurality of tubular members arranged in a serial fashion, the tubular members each including a flexible zigzag shaped wire having a plurality of alternating first and second apexes; a stent collapsing mechanism including a first plurality of longitudinal wires connected to the first apexes, and a second plurality of longitudinal wires connected to the second apexes; wherein proximal ends of the first plurality of longitudinal wires extend beyond a proximal end of the stent body and are operably connected to each other; and wherein distal ends of the second plurality of longitudinal wires extend beyond a distal end of the stent body and are operably connected to each other.

In a third aspect, a non-foreshortening, axial tension constrainable stent is provided having an elongated tubular body having a proximal portion, a distal portion, and a lumen extending between the proximal portion and distal portion; a first non-foreshortening, axial tension constrainable means in communication with at least a portion of the elongated tubular body; a second non-foreshortening, axial tension constrainable means in communication with at least a portion of the elongated tubular body different from the first non-foreshortening, axial tension constrainable means; a third non-foreshortening, axial tension constrainable means connected to the proximal portion; a fourth non-foreshortening, axial tension constrainable means connected to the distal portion; wherein the first non-foreshortening, axial tension constrainable means, second non-foreshortening, axial tension constrainable means, third non-foreshortening, axial tension constrainable means, and fourth non-foreshortening, axial tension constrainable means are configured to collapse the non-foreshortening, axial tension constrainable stent when opposite axial forces are applied to the third non-foreshortening means and the fourth non-foreshortening, axial tension constrainable means; and wherein the first non-foreshortening, axial tension constrainable means, second non-foreshortening, axial tension constrainable means, third non-foreshortening, axial tension constrainable means, and fourth non-foreshortening, axial tension constrainable means are configured to maintain the length of the non-foreshortening, axial tension constrainable stent as about the same when in the collapsed state and an expanded state.

In a fourth aspect, a method of manufacturing a non-foreshortening, axial tension constrainable stent is provided including creating a zigzag pattern from a plurality of individual wires wherein each individual wire forming each zigzag section overlaps at an end and wherein each zigzag has an apex directed in a proximal direction or a distal direction; heat-setting the wires where they are biased to assume the zigzag pattern; tying a first suture to each apex directed in the proximal direction; tying a second suture to each apex directed in the distal direction; looping a first purse string suture through a plurality of loops of the first suture; and looping a second purse string suture through a plurality of loops of the second suture.

BRIEF DESCRIPTION OF THE SEVERAL VIEWS OF THE DRAWINGS

The embodiments will be further described in connection with the attached drawing figures. It is intended that the drawings included as a part of this specification be illustrative of the exemplary embodiments and should in no way be considered as a limitation on the scope of the invention. Indeed, the present disclosure specifically contemplates other embodiments not illustrated but intended to be included in the claims.

DETAILED DESCRIPTION OF PRESENTLY PREFERRED EMBODIMENTS

Figure 1:
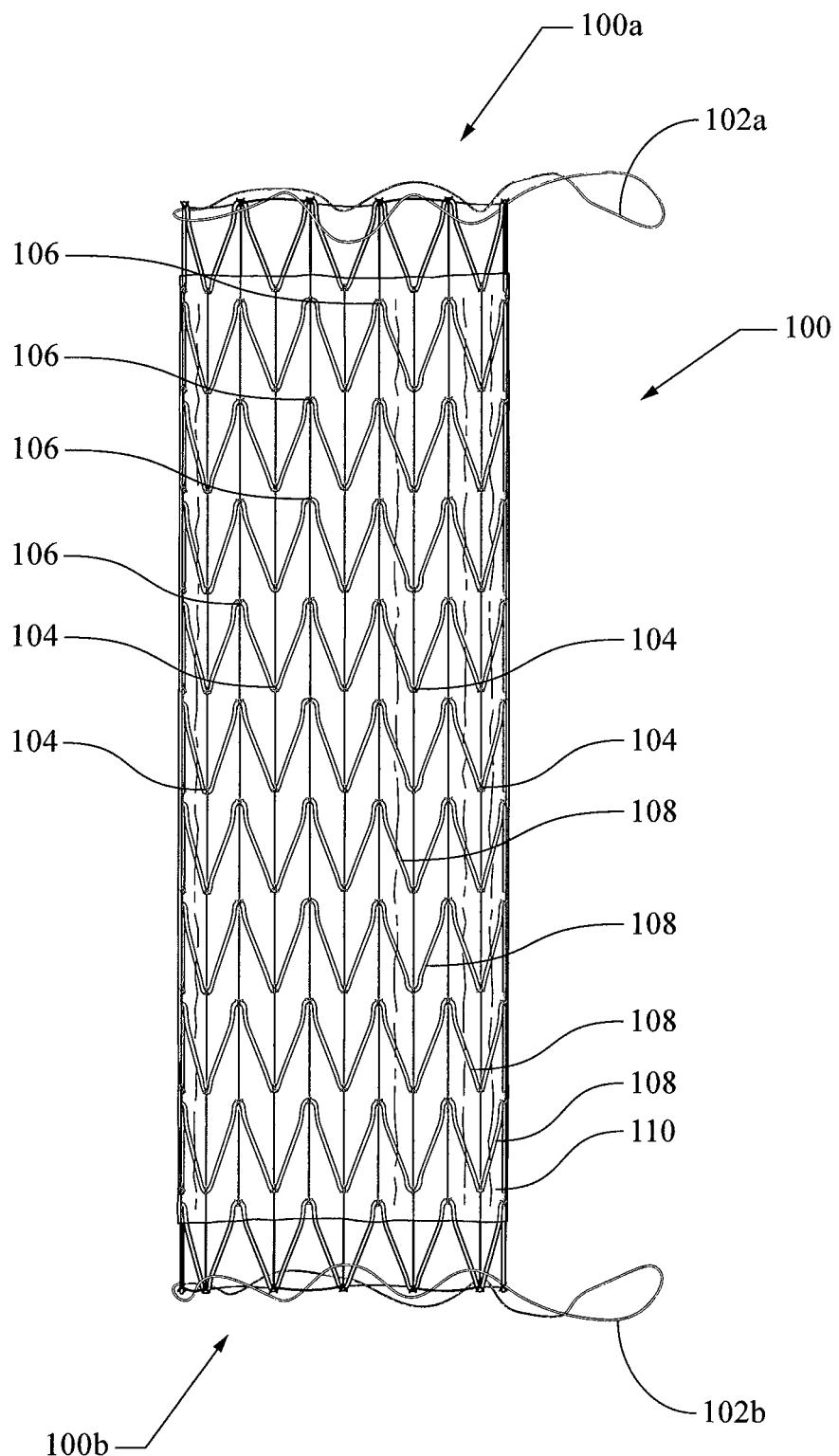
FIG. 1 illustrates an exemplary side view of a self expanding non-foreshortening, axial tension constrainable stent in an expanded state.

The exemplary embodiments illustrated herein provide exemplary apparatuses and methods for addressing foreshortening and constrainment in a self expanding stent. The present invention is not limited to those embodiments described herein, but rather, the disclosure includes all equivalents including those of different shapes, sizes, and configurations, including but not limited to, other types of stents. For example, the principles herein can be applied to other types of stents, including but not limited to, self expanding metal stents, self expanding laser cut peripheral artery stents, laser cut balloon expandable stents, laser cut self expanding stents, woven wire stents, the ZILVER® (Wilson-Cook Medical Inc.), and the EVOLUTION® (Wilson-Cook Medical Inc.). The devices and methods can be used in any field benefiting from a stent. Additionally, the devices and methods are not limited to being used with a human being, others are contemplated, including but not limited to, animals.

A more detailed description of the embodiments will now be given with reference to FIGS. 1-4. Throughout the disclosure, like reference numerals and letters refer to like elements. The present disclosure is not limited to the embodiments illustrated; to the contrary, the present disclosure specifically contemplates other embodiments not illustrated but intended to be included in the claims.

FIG. 1 illustrates an exemplary side view of a self expanding non-foreshortening, axial tension constrainable stent 100 in an expanded state having proximal portion 100a and distal portion 100b. Stent 100 addresses, inter alia, the problem of foreshortening, which may result in improper stent placement, and provides for axial constrainment useful for, inter alia, deployment as well as post-deployment collapsing for repositioning and removal of stent 100. Accordingly the length of stent 100 in a collapsed state (illustrated in FIG. 2) is about equal to the length of stent 100 in an expanded state (illustrated in FIG. 1), although it is not required that they be exactly equal.

Stent 100 is preferably, although not required, self-expanding and has the tendency to radially collapse when a longitudinal force is applied to the ends of the stent. By way of non-limiting example, stent 100 may be formed as a woven mesh formed from a metal or polymer or a laser cut pattern formed in a metal stent. Stent 100 may also be formed from a bioabsorbable material. An example of a woven stent is the EVOLUTION® (Wilson-Cook Medical Inc.).

Stent 100 includes a plurality of zigzags 108 (illustrated in a horizontal configuration; other configurations are contemplated) arranged in serial fashion made from nickel titanium (nitinol) wires although other materials are contemplated, including but not limited to, stainless steel and any medical-grade material having properties similar to nitinol such that the material is configurable into a biased position and when out from that position is biased to resume the initial biased position.

The stent can be used in conjunction with a delivery device that, for example, uses an axial expanding rigid central core (to which either end of the stent is tethered to), to apply a longitudinal (axial tensile) mechanical force to either end of the stent, in order to collapse the stent diameter and to constrain it down. For example, stent 100 can be delivered and placed using a variety of means, including but not limited to, the system described in U.S. Patent Publication No. 2011-0190865 A1, entitled "Mechanically Expandable Delivery and Dilation Systems," and incorporated in its entirety herein by reference. Stent 100 does not foreshorten when constrained by the introducer described in U.S. Patent Publication No. 2011-0190865 A1. Stent 100 can be properly placed without the use of a sheath.

It has been discovered that applying a plurality of non-foreshortening, axial tension constrainable means, such as sutures (or wires), in strategic configurations can provide for a non-foreshortening, axial tension constrainable stent.

Stent 100 includes sutures 106 that are tried at the apex of the upward-pointing (proximal-pointing) zigzag 108 peaks, although other configurations are contemplated depending upon the design or configuration of the stent. Sutures 104 are tied and knotted at the apex of the downward-pointing (distal-pointing) zigzag 108 peaks, although other configurations are contemplated depending upon the design or configuration of the stent. Suture 102a, in the proximal portion 100a, is then looped through the loops that result from suture 106 and is tied in a purse string configuration, to form a double purse string configuration, although other configurations are contemplated depending upon the design or configuration of the stent. Suture 102b, in the distal portion 100b, is looped through the loops that result from suture 104, and is tied in a purse string configuration, to form a double purse string configuration, although other configurations are contemplated depending upon the design or configuration of the stent. Optionally, silicone membrane 110 is applied over stent, for example, to prevent tissue in-growth, although other materials are contemplated, including but not limited, other medical-grade materials, biodegradable materials, chemicals, drugs, no coating, or a partial coating.

Sutures 102a, 102b, 104, and 106 are made from nitinol or other medical grade material, and ideally sutures 102a, 102b, 104, and 106 would be non-metallic (although a multi strand wire may provide sufficient flexibility), so as to have sufficient flexibility and a low column strength permitting the stent to bend, including but not limited to, a polymer such as nylon or polyethylene. Indeed, it is also contemplated that sutures can be made from one or more wires. It is understood that sutures 102a, 102b forming purse strings, can be made from a material that is the same or different from those of sutures 104 and 106. It is also contemplated that sutures 102a, 102b, 104, and 106 may be made from common suture material as known in the art, for example polyester suture such as 4-0 Tevdek®, silk, ultra high molecular weight polyethylene (UHMPE) and the like, and they may be monofilament, braided, twisted, or multifilament. Additionally, in some embodiments, sutures 102a, 102b, 104, and 106 may be made from biodegradable materials; a number of bioabsorbable homopolymers, copolymers, or blends of bioabsorbable polymers are known in the medical arts. These include, but are not necessarily limited to, polyesters including poly-alpha hydroxy and poly-beta hydroxy polyesters, polycaprolactone, polyglycolic acid, polyether-esters, poly(p-dioxanone), polyoxaesters; polyphosphazenes; polyanhydrides; polycarbonates including polytrimethylene carbonate and poly(iminocarbonate); polyesteramides; polyurethanes; polyisocyantes; polyphosphazines; polyethers including polyglycols polyorthoesters; expoxy polymers including polyethylene oxide; polysaccharides including cellulose, chitin, dextran, starch, hydroxyethyl starch, polygluconate, hyaluronic acid; polyamides including polyamino acids, polyester-amides, polyglutamic acid, poly-lysine, gelatin, fibrin, fibrinogen, casein, collagen.

The dimensions of stent 100 are dependent on its application. For example, when used as a biliary stent, sutures 102a and 102b are about 40 mm long, about 0.3 mm in diameter, although other dimensions are contemplated depending upon the design or configuration of the stent. Stent 100, when in a collapsed or expanded state, is about 80 mm long, although other dimensions are contemplated depending upon the area to be treated and the needs of the patient. Stent 100, has about a 3 mm diameter when in a collapsed state, and it has about a 10 mm diameter when in an expanded state, although other dimensions are contemplated depending upon the area to be treated and the needs of the patient.

Zigzags wires 108 are about 0.15 mm in diameter although other dimensions are contemplated. It is recognized that the angle of the zigzag pattern and the number of peaks around the circumference will control the force required to collapse the stent. The angle of the zigzag pattern and the number of peaks around the circumference together with the degree of overlap will also control the flexibility of the stent.

Although preferably sized for use in the gastrointestinal and biliary region, other dimensions, uses, and locations are contemplated depending upon the needs of the patient and the area to be treated. Indeed, other configurations of non-foreshortening, axial tension constrainable means are contemplated.

Figure 1A:
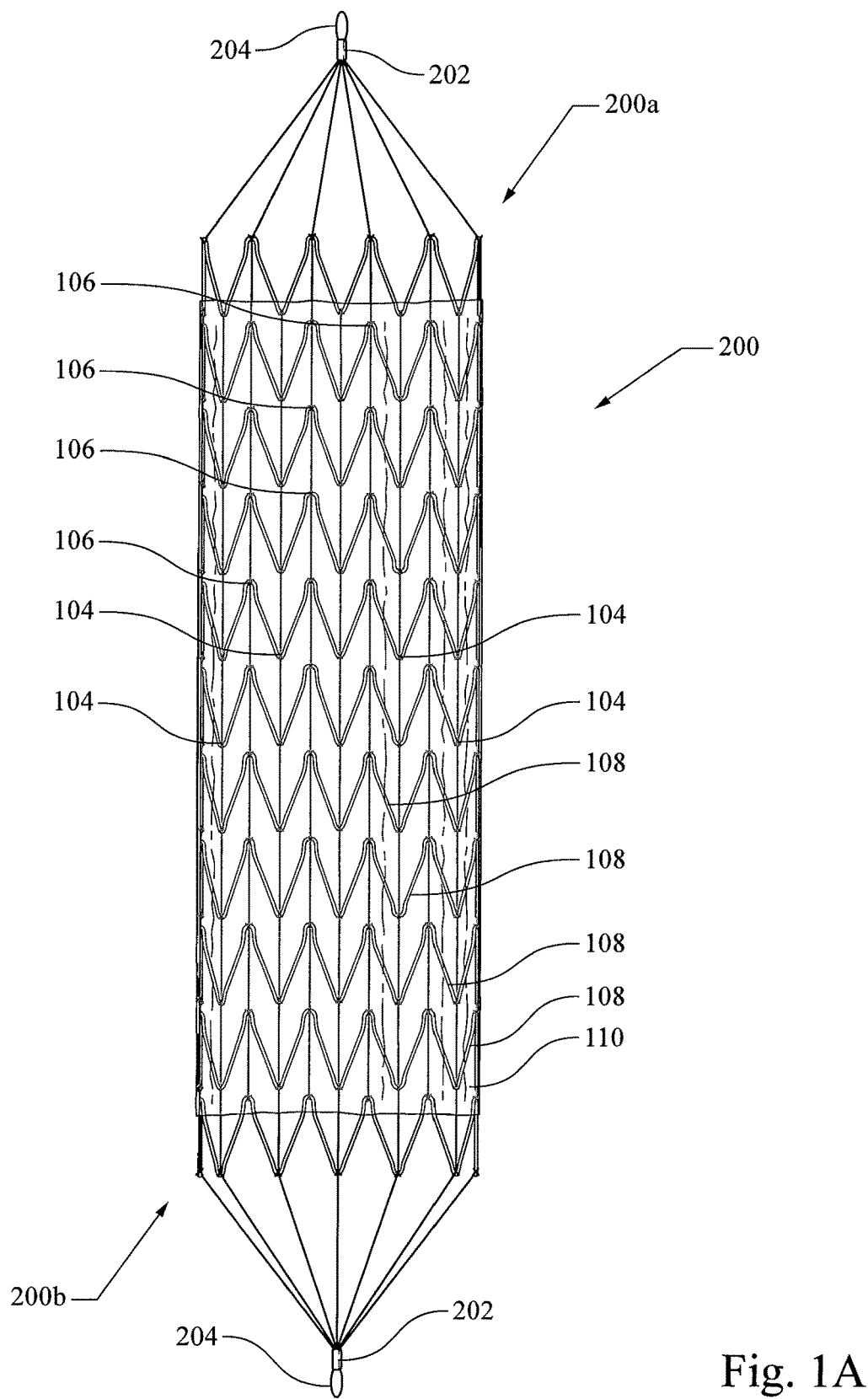
FIG. 1A illustrates an alternate embodiment of a self expanding non-foreshortening, axial tension constrainable stent in an expanded state.

FIG. 1A illustrates an alternate embodiment of a self expanding non-foreshortening, axial tension constrainable stent 200 in an expanded state. Unlike stent 100 (illustrated in FIGS. 1, 2), stent 200 (illustrated in FIG. 1A) does not have purse string sutures. Instead, the longitudinal sutures 104, 106 extend beyond proximal end 200a and distal end 200b of stent 200, respectively, and are operably connected to each other by way of cannula 202 having grasping loop 204. Other means for connection are contemplated, including but not limited to, a knot.

Figure 2:
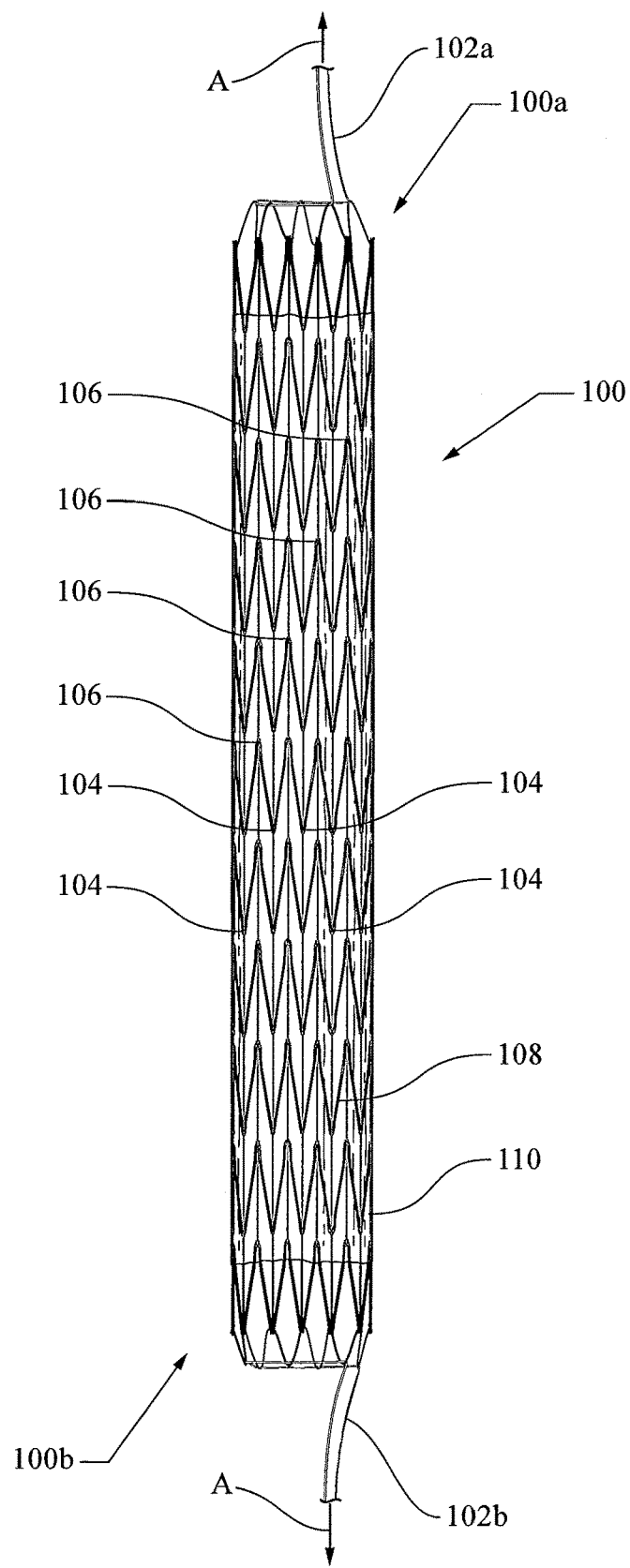
FIG. 2 illustrates an exemplary side view of a self expanding non-foreshortening, axial tension constrainable stent in a collapsed state.

FIG. 2 illustrates an exemplary side view of a self expanding non-foreshortening, axial tension constrainable stent 100 in a collapsed state. When purse string sutures 102a and 102b are pulled in the direction of Arrows A by an axial force, stent 100 collapses without lengthening. When the axial force is removed, as illustrated in FIG. 1, stent 100 expands without foreshortening.

Figure 3:
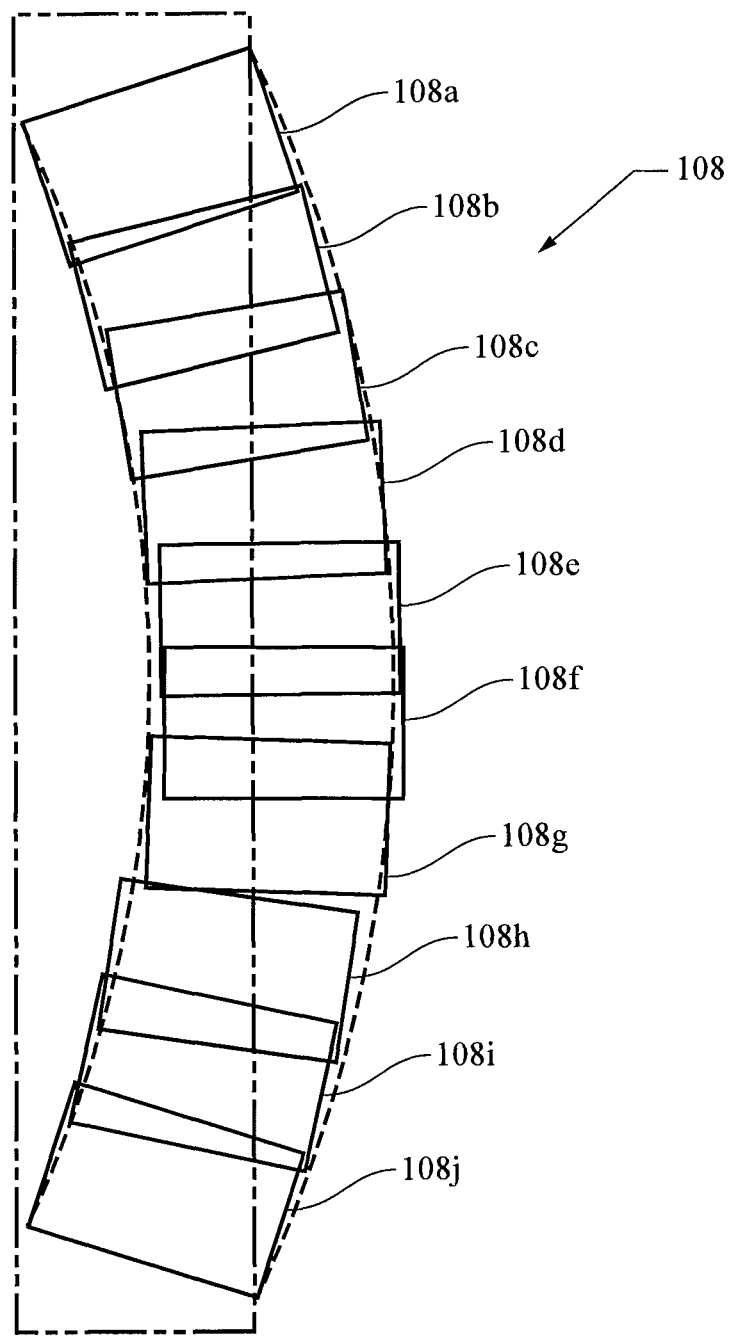
FIG. 3 illustrates an exemplary flexibility of an exemplary self expanding non-foreshortening, axial tension constrainable stent.

FIG. 3 illustrates an exemplary schematic representation of the flexibility of an exemplary self expanding non-foreshortening, axial tension constrainable stent 100. Each rectangle 108a-j represents a nitinol zigzag 108 as illustrated in FIGS. 1-2. Because sutures 104, 106 have extremely low column strength, stent 100 easily flexes as illustrated in FIG. 3.

It can seen that applying the principles herein would overcome, for example, the challenges associated with deploying very long stents from a sheath while still maintaining stent flexibility because, for example, stent 100, 200 can be constrained without the use of a sheath. Additionally, because stent 100, 200 is constrainable using non-foreshortening, axial tension constrainable means, such as purse string sutures 102a, 102b, or connection means 202, 204, stent 100, 200 can be easily removed from or repositioned within a lumen by applying an axial force in the direction of Arrows A (as illustrated in FIG. 2). Additionally, because stent 100, 200 has a low columnar strength, it is contemplated that stent 100, 200 may have better resistance to migration for applications where, for example, peristalsis is present.

Figure 4:
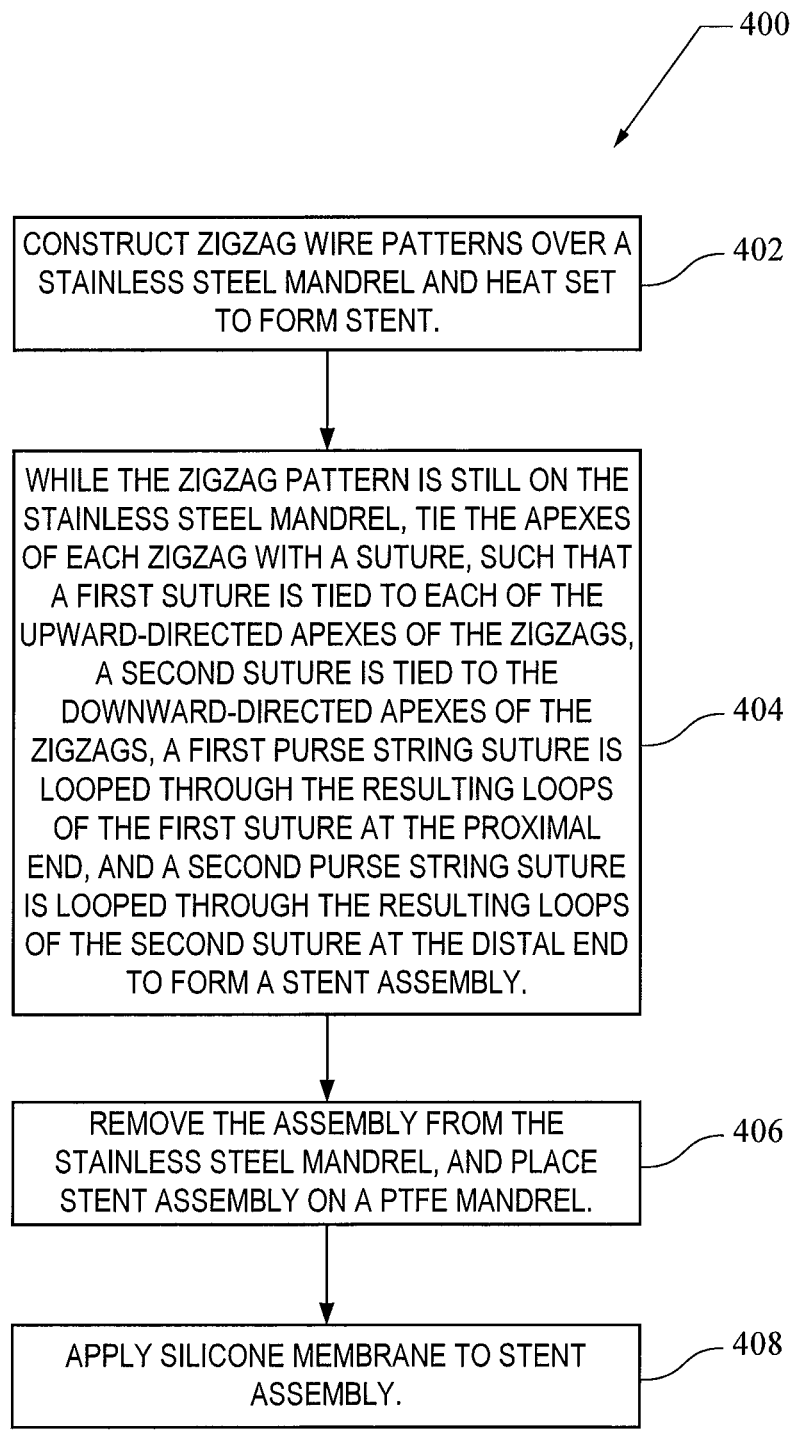
FIG. 4 illustrates an exemplary process flow chart for manufacturing an exemplary non-foreshortening, axial tension constrainable stent.

FIG. 4 illustrates an exemplary process flow chart for manufacturing an exemplary self expanding non-foreshortening, axial tension constrainable stent 400. At block 402, a zigzag pattern is created using, preferably, although in no way required, nitinol wires over a first mandrel made from, for example, stainless steel, nitinol, or other materials. It is preferred, although not required, that each individual wire forming each zigzag section overlap at the end. An overlap is preferred but not required. Zigzag pattern is created over mandrel and is heat-set such that wires are biased to assume the zigzag pattern created.

After heat-setting and while the zigzag pattern is still on the first mandrel, the apex of each zigzag is tied with a suture at block 404, such that a first suture is tied to each of the upward-pointing (proximal-pointing) apexes of the zigzags, a second suture is tied to the downward-pointing (distal-pointing) apexes of the zigzags, a first purse string suture is looped though the resulting loops of the first suture at the proximal end, and a second purse string suture is looped through the resulting loops of the second suture at the distal end to form a stent assembly.

The assembled stent is then removed from the first mandrel and placed onto a second mandrel, which is preferably, although not required, made from polytetrafluoroethylene (PTFE) at block 406.

An optional silicone membrane (or other coating, or partial coating, or no coating) is applied over the stent assembly at block 408.

From the foregoing, it can be seen that a non-foreshortening, axial tension constrainable stent can be achieved from the discovery of strategically configured axial tension constrainable means, such as sutures such that when an axial force is applied to the proximal and distal sutures, the stent collapses, and when the axial force to the proximal and distal sutures is released, the stent expands without foreshortening. Other configurations are contemplated depending upon the design or configuration of the stent, the needs of the patient, or the area to be treated.

What is claimed is:

1. A non-foreshortening, axial tension constrainable stent comprising:
    a proximal portion and a distal portion;
    a plurality of non-woven wires configured in a plurality of individual rows, wherein each row is configured into a plurality of zigzags formed from a single non-woven wire, wherein the rows together comprise a cylindrical shape having a lumen extending between the proximal portion and the distal portion, and wherein each of the plurality of zigzags comprise a plurality of first apexes pointing towards the proximal portion and a plurality of second apexes pointing towards the distal portion;
    a plurality of longitudinally oriented first sutures in communication with the first apexes of the zigzags wherein the proximal-most portions of the first sutures comprise a plurality of first loops;

a plurality of longitudinally oriented second sutures in communication with the second apexes of the zigzags wherein the distal-most portions of the second sutures comprise a plurality of second loops;

a first purse string suture woven through the plurality of first loops; and a second purse string suture woven through the plurality of second loops;

wherein the first sutures and second sutures each comprise a flexible and non-foreshortening material that is configured to apply an axially oriented tensile force to the first and second apexes of the zigzags; and wherein the first purse string suture and the second purse string suture are configured to collapse the plurality of zigzags when an opposite axial force is applied without a sheath to each of the first purse string suture and the second purse string suture by pulling the first and second sutures in an opposite longitudinal direction so as to move the plurality of first apexes and the plurality of second apexes in opposite longitudinal directions.

2. The non-foreshortening, axial tension constrainable stent of claim 1, wherein a collapsed length of the non-foreshortening, axial tension constrainable stent is equal to an uncollapsed length of the non-foreshortening, axial tension constrainable stent.

3. The non-foreshortening, axial tension constrainable stent of claim 1, wherein the zigzags overlap.

4. The non-foreshortening, axial tension constrainable stent of claim 1, wherein at least one of the plurality of first sutures, the plurality of second sutures, the first purse string suture, or the second purse string suture comprises nickel titanium (nitinol).

5. The non-foreshortening, axial tension constrainable stent of claim 1, wherein at least one of the plurality of first sutures, the plurality of second sutures, the first purse string suture, or the second purse string suture comprises stainless steel.

6. The non-foreshortening, axial tension constrainable stent of claim 1, wherein at least one of the plurality of wires comprises nitinol.

7. The non-foreshortening, axial tension constrainable stent of claim 1, wherein one of the plurality of wires has a diameter of 0.15 mm.

8. The non-foreshortening, axial tension constrainable stent of claim 1, wherein one of the first purse string suture and the second purse string suture are 40 mm long.

9. The non-foreshortening, axial tension constrainable stent of claim 1, wherein one of the first purse string suture and the second purse string suture have a 0.3 mm diameter.

10. The non-foreshortening, axial tension constrainable stent of claim 1, wherein the non-foreshortening, axial tension constrainable stent in the collapsed state has a 3 mm diameter.

11. The non-foreshortening, axial tension constrainable stent of claim 1, wherein the non-foreshortening, axial tension constrainable stent in an expanded state has about a 10 mm diameter.

12. A stent comprising:

a non-woven stent body formed from a plurality of separate and spaced apart tubular members arranged in a serial fashion along a longitudinal axis of the stent body, the tubular members each comprising a flexible zigzag shaped wire having a plurality of alternating first and second apexes, wherein the plurality of first apexes points towards the proximal portion and the plurality of second apexes points towards the distal portion;

a stent collapsing mechanism comprising a first plurality of flexible longitudinal wires connected to the first apexes of each of the plurality of tubular members, and a second plurality of flexible longitudinal wires connected to the second apexes of each of the plurality of tubular members, the first and second plurality of longitudinal wires being disposed parallel to the longitudinal axis of the stent body;

wherein a proximal end of the first plurality of flexible longitudinal wires extends beyond a proximal end of the stent body and are operably connected to each other;

wherein a distal end of the second plurality of flexible longitudinal wires extends beyond a distal end of the stent body and are operably connected to each other; and wherein the stent is configured to be collapsed along the length thereof by applying opposing axial forces without a sheath to the operable connections of the first and second plurality of flexible longitudinal wires, the opposing axial forces causing axially oriented tensile forces to be applied by the first and second plurality of flexible longitudinal wires so as to cause the first and second apexes of each zigzag to move in opposite longitudinal directions.

13. The stent of claim 12, wherein a collapsed length of the stent is equal to an uncollapsed length of the stent.

14. A non-foreshortening, axial tension constrainable stent comprising:

an elongated tubular body having a proximal portion, a distal portion, and a lumen extending between the proximal portion and distal portion, the elongated tubular body comprising a plurality of spaced apart non-woven metallic structures, wherein the plurality of spaced apart non-woven metallic structures each comprise a zigzag formed from a single non-woven wire, and wherein the zigzags each comprise a plurality of first apexes pointing towards the proximal portion and a plurality of second apexes pointing towards the distal portion;

a first non-foreshortening, axial tension constrainable means in communication with the first apexes of the zigzags of the elongated tubular body;

a second non-foreshortening, axial tension constrainable means in communication with the second apexes of the zigzags of the elongated tubular body;

a third non-foreshortening, axial tension constrainable means operably connected to the proximal portion of the stent at a location adjacent to a proximal end of the first non-foreshortening, axial tension constrainable means;

a fourth non-foreshortening, axial tension constrainable means operably connected to the distal portion of the stent at a location adjacent to a distal end of the second non-foreshortening, axial tension constrainable means;

wherein the first non-foreshortening, axial tension constrainable means and the second non-foreshortening, axial tension constrainable means each comprise a longitudinally oriented non-metallic flexible structure coupled to each of the non-woven metallic structures of the elongated tubular body;

wherein the third non-foreshortening, axial tension constrainable means and the fourth non-foreshortening, axial tension constrainable means each comprise a circumferentially oriented non-metallic structure;

wherein the first non-foreshortening, axial tension constrainable means, second non-foreshortening, axial tension constrainable means, third non-foreshortening, axial tension constrainable means, and fourth non-foreshortening, axial tension constrainable means are configured to collapse the non-foreshortening, axial tension constrainable stent when opposite axial forces are applied without a sheath to the third non-foreshortening, axial tension constrainable means and the fourth non-foreshortening, axial tension constrainable means; and wherein the first non-foreshortening, axial tension constrainable means, second non-foreshortening, axial tension constrainable means, third non-foreshortening, axial tension constrainable means, and fourth non-foreshortening, axial tension constrainable means are configured to maintain the length of the non-foreshortening, axial tension constrainable stent as about the same when in the collapsed state and an expanded state.

15. The non-foreshortening, axial tension constrainable stent of claim 14, wherein the first, second, third, and fourth non-foreshortening, axial tension constrainable means are each sutures.

16. The non-foreshortening, axial tension constrainable stent of claim 1, wherein the plurality of rows of zigzags are arranged in a non-overlapping configuration.

17. The non-foreshortening, axial tension constrainable stent of claim 1, wherein the plurality of longitudinal first sutures and plurality of longitudinal second sutures are disposed parallel to a longitudinal central axis of the stent.

* * * * *